United States Patent
Wu et al.

(10) Patent No.: US 11,311,245 B2
(45) Date of Patent: Apr. 26, 2022

(54) ECG NOISE-FILTERING DEVICE

(71) Applicant: Quanta Computer Inc., Taoyuan (TW)

(72) Inventors: Pei-Sheng Wu, Taoyuan (TW);
Yu-Siang Wang, Taoyuan (TW);
Peng-Zhe Tsai, Taoyuan (TW);
Yung-Ming Chung, Taoyuan (TW)

(73) Assignee: QUANTA COMPUTER INC., Taoyuan (TW)

( * ) Notice: Subject to any disclaimer, the term of this patent is extended or adjusted under 35 U.S.C. 154(b) by 0 days.

(21) Appl. No.: 17/107,553

(22) Filed: Nov. 30, 2020

(65) Prior Publication Data
US 2022/0071565 A1 Mar. 10, 2022

(30) Foreign Application Priority Data

Sep. 10, 2020 (TW) .................................. 109131018

(51) Int. Cl.
*A61B 5/00* (2006.01)
*A61B 5/316* (2021.01)
*A61B 5/366* (2021.01)

(52) U.S. Cl.
CPC ............ *A61B 5/7214* (2013.01); *A61B 5/316* (2021.01); *A61B 5/366* (2021.01); *A61B 5/726* (2013.01)

(58) Field of Classification Search
CPC ....... A61B 5/7214; A61B 5/366; A61B 5/316; A61B 5/726
See application file for complete search history.

(56) References Cited

U.S. PATENT DOCUMENTS

| 9,936,919 | B2 | 4/2018 | Baxi et al. | |
| 2011/0319777 | A1* | 12/2011 | Mehrotra | A61B 5/0006 600/509 |
| 2017/0086752 | A1* | 3/2017 | Baxi | A61B 5/0245 |
| 2021/0386354 | A1* | 12/2021 | Crespin | G06N 3/08 |

FOREIGN PATENT DOCUMENTS

TW 201717845 A 6/2017

OTHER PUBLICATIONS

Chinese language office action dated Feb. 3, 2021, issued in application No. TW 109131018.

* cited by examiner

*Primary Examiner* — Catherine M Voorhees
*Assistant Examiner* — Roland Dinga
(74) *Attorney, Agent, or Firm* — McClure, Qualey & Rodack, LLP

(57) ABSTRACT

An Electrocardiography (ECG) noise-filtering device is provided in the invention. The ECG device includes a filter and a calculation circuit. The filter receives a first ECG signal and performs a Savitzky-Golay algorithm to generate a second ECG signal. The calculation circuit is coupled to the filter to receive the second ECG signal and processes the second ECG signal according to a Stationary Wavelet Transform (SWT) algorithm to generate a noise signal, and subtracts the noise signal from the second ECG signal to filter the noise signal in the first ECG signal.

10 Claims, 3 Drawing Sheets

ECG NOISE-FILTERING DEVICE

CROSS REFERENCE TO RELATED APPLICATIONS

This application claims priority of TW Patent Application No. 109131018 filed on Sep. 10, 2020, the entirety of which is incorporated by reference herein.

BACKGROUND OF THE INVENTION

Field of the Invention

The invention generally relates to electrocardiography (ECG) noise-filtering technology, and more particularly, to an ECG noise-filtering technology in which the combination of the Savitzky-Golay algorithm and the Stationary Wavelet Transform (SWT) algorithm is used to filter irregular noise in ECG signals.

Description of the Related Art

As technology progresses and medical techniques improve, there are greater requirements for measurements and analysis of the biological signals from the human body. Electrocardiography (ECG) is a medical diagnostic technology in which the electronic physiological activity of the heart is recorded through the electrodes on the skin and recorded in time. ECG signals may experience interference due to different noises (e.g. powerline noise, wire (or electrode) motion noise, Electromyography (EMG) noise, and base-line-wander noise).

Traditionally, a high-pass filter, a low-pass filter, a band-pass filter or a band-rejection filter is used to filter such noise. However, the low-pass filter, the band-pass filter or the band-rejection filter may only filter noises within a specific frequency, and the attenuation rate cannot be immediately adjusted. Therefore, when the attenuation rate of the filter is too high, the real ECG signal may be also be filtered.

BRIEF SUMMARY OF THE INVENTION

An Electrocardiography (ECG) noise-filtering device is provided to overcome the problems mentioned above.

An embodiment of the invention provides an Electrocardiography (ECG) noise-filtering device. The ECG device includes a filter and a calculation circuit. The filter receives a first ECG signal and performs an algorithm to generate a second ECG signal. The calculation circuit is coupled to the filter to receive the second ECG signal and processes the second ECG signal to generate a noise signal, and subtracts the noise signal from the second ECG signal to filter the noise signal in the first ECG signal.

According to an embodiment of the invention, the filter is a Savitzky-Golay filter.

According to an embodiment of the invention, the calculation circuit comprises a first calculation circuit. The first calculation circuit is coupled to the filter. After the first calculation circuit receives the second ECG signal, the first calculation circuit performs a SWT calculation on the second ECG signal obtained during the initial period according to the SWT algorithm, obtains the second ECG signal obtained in the initial period in the lowest level, and performs a QRS detection on the second ECG signal obtained during the initial period in the lowest level to generate a QRS template signal.

According to an embodiment of the invention, the calculation circuit further comprises a first SWT circuit. The first SWT circuit is coupled to the filter. After the initial period, the first SWT circuit performs an SWT algorithm with a first number of levels on the second ECG signal received from the filter, and filters the second ECG signal in the highest level to output third ECG signals with the first number of levels.

According to an embodiment of the invention, the calculation circuit further comprises an inverse SWT (ISWT) circuit. The ISWT circuit is coupled to the first SWT circuit to receive the third ECG signals with the first number of levels. The ISWT circuit performs an ISWT algorithm on the third ECG signals with the first number of levels to output a fourth ECG signal.

According to an embodiment of the invention, the calculation circuit further comprises a second SWT circuit. The second SWT circuit is coupled to the ISWT circuit to receive the fourth ECG signal. The second SWT circuit performs an SWT algorithm with a second number of levels on the fourth ECG signal to generate fifth ECG signals with the second number of levels.

According to an embodiment of the invention, the calculation circuit further comprises a second calculation circuit. The second calculation circuit is coupled to the first calculation circuit and the second SWT circuit to receive the QRS template signal and the fifth ECG signals with the second number of levels, wherein the second calculation circuit performs a correlation calculation on the QRS template signal and the fifth ECG signal in the lowest level to filter QRS wave signals of fifth ECG signals in each level.

According to an embodiment of the invention, in the correlation calculation, the second calculation circuit compares the QRS template signal to the fifth ECG signal in the lowest level, wherein the second calculation circuit regards the parts of the fifth ECG signal in the lowest level whose correlation with the QRS template signal is higher than a threshold as the QRS wave signals of the fifth ECG signal in the lowest level.

According to an embodiment of the invention, the second calculation circuit performs a PT-wave removal operation on the fifth ECG signals with lower frequencies whose QRS wave signals have been removed to filter P-wave signals and T-wave signals in the fifth ECG signals with lower frequencies.

According to an embodiment of the invention, after the second calculation circuit filters the P-wave signals and the T-wave signals in the fifth ECG signals with lower frequencies, the second calculation circuit performs an ISWT algorithm to generate a noise signal.

According to an embodiment of the invention, the calculation circuit further comprises a subtraction circuit. The subtraction circuit is coupled to the second calculation circuit. The subtraction circuit receives the fourth ECG signal and the noise signal, and subtracts the noise signal from the fourth ECG signal to filter the noise signal of the first ECG signal.

Other aspects and features of the invention will become apparent to those with ordinary skill in the art upon review of the following descriptions of specific embodiments of intravenous infusion detection device and method.

BRIEF DESCRIPTION OF THE DRAWINGS

The invention will become more fully understood by referring to the following detailed description with reference to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
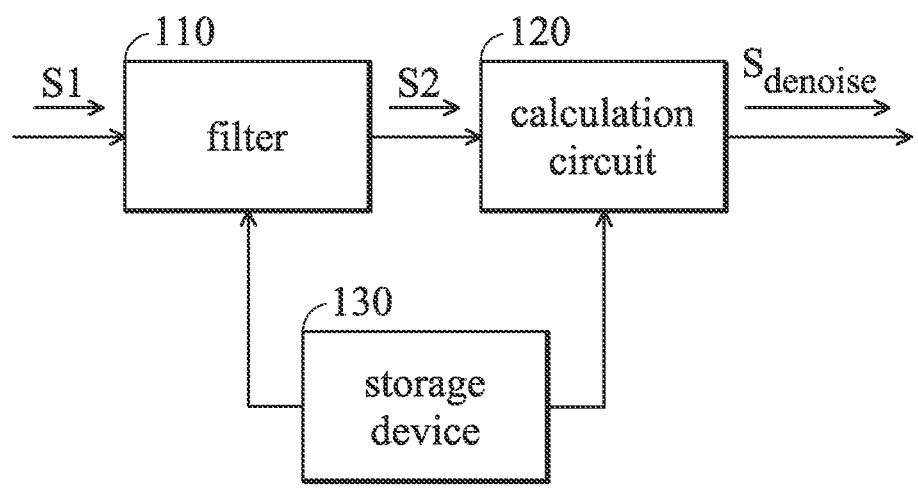
FIG. 1 is a block diagram of an electrocardiography (ECG) noise-filtering device 100 according to an embodiment of the invention.

FIG. 1 is a block diagram of an electrocardiography (ECG) noise-filtering device 100 according to an embodiment of the invention. As shown in FIG. 1, the intravenous infusion detection device 100 may comprise a filter 110, a calculation circuit 120 and a storage device 150. It should be noted that FIG. 1 presents a simplified block diagram in which only the elements relevant to the invention are shown. However, the invention should not be limited to what is shown in FIG. 1. The ECG noise-filtering device 100 may also comprise other elements. According to an embodiment of the invention, the filter 110 and the calculation circuit 120 may be integrated into a chip.

According to the embodiments of the invention, the storage device 130 may be a volatile memory (e.g. Random Access Memory (RAM)), or a non-volatile memory (e.g. flash memory, Read Only Memory (ROM)), a hard disk, or a combination of the above memory devices. The storage device 130 may store the files and data which are performed to filter the ECG noise.

According to an embodiment of the invention, the filter 100 may be a Savitzky-Gokay filter. The filter 110 may receive a first ECG signal (i.e. original ECG signal) S1. The first ECG signal (i.e. original ECG signal) S1 may be the measured ECG signal of the respondent which is obtained through an ECG signal extracting device (not shown in figures). In addition, the first ECG signal S1 received by the filter 110 may be the ECG signal which has been sampled (e.g. the original ECG signal is sampled in 256 Hz sampling rate to generate a first ECG signal S1, but the invention should not be limited thereto).

The filter 110 may perform a Savitzky-Golay algorithm for the first ECG signal S1 to cancel the high-frequency noise in the first ECG signal S1, e.g. the EMG noise. The EMG noise may be the EMG signal which is generated from the motion of the human muscle. According to the embodiments of the invention, after the filter 110 filters the high-frequency noise in the first ECG signal S1, the filter 110 may output a second ECG signal S2 (i.e. the first ECG signal S1 has been processed by the filter 110) to the calculation circuit 120. According to another embodiment of the invention, the operations of the filter 110 also can be realized by a processor performing the related codes. The related codes may be stored in the storage device 130.

Figure 2:
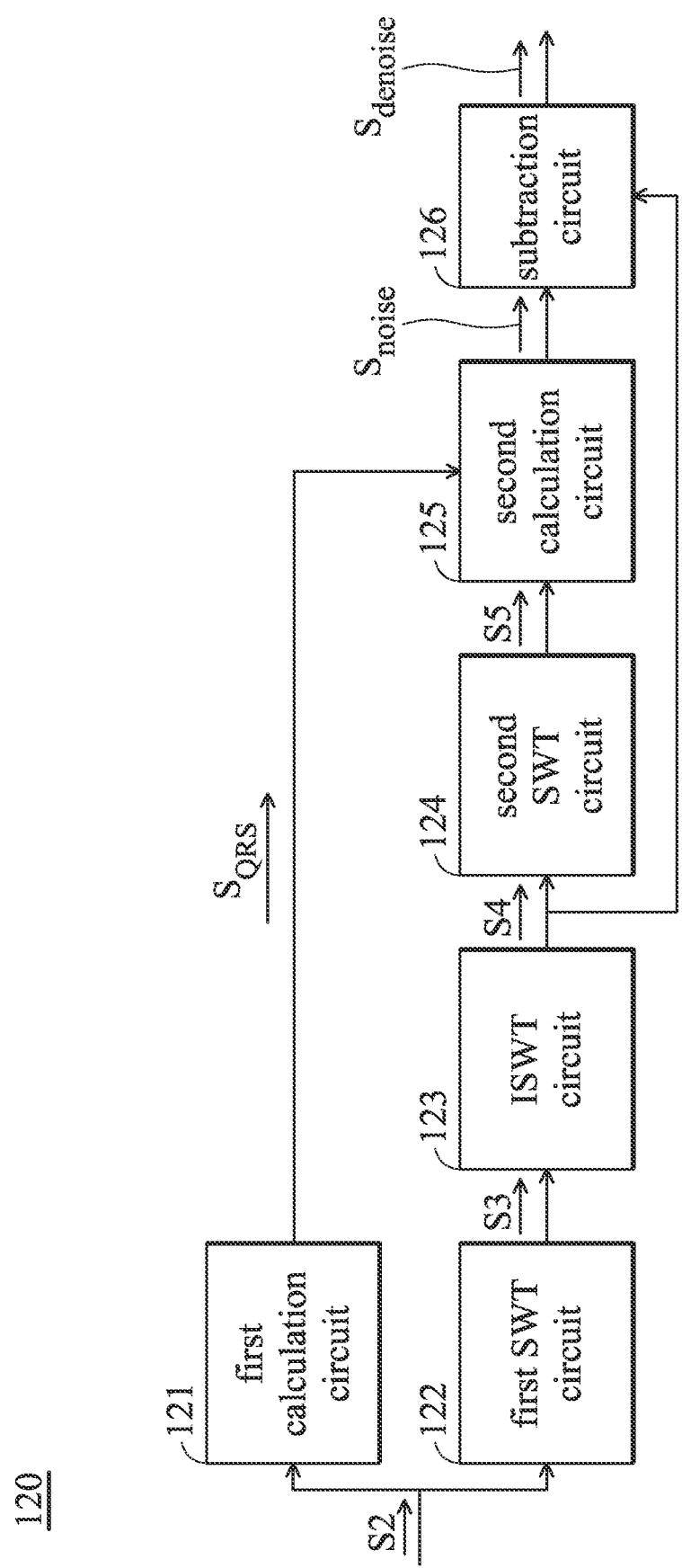
FIG. 2 is a block diagram of a calculation circuit 120 according to an embodiment of the invention.

FIG. 2 is a block diagram of a calculation circuit 120 according to an embodiment of the invention. As shown in FIG. 2, the calculation circuit 120 may comprise a first calculation circuit 121, a first stationary wavelet transform (SWT) circuit 122, an inverse SWT (ISWT) circuit 123, a second SWT circuit 124, a second calculation circuit 125 and a subtraction circuit 126. It should be noted that FIG. 2 presents a simplified block diagram in which only the elements relevant to the invention are shown. However, the invention should not be limited to what is shown in FIG. 2. The calculation circuit 120 may also comprise other elements. According to another embodiment of the invention, the operations of the calculation circuit 120 also can be realized by a processor performing the related codes. The related codes may be stored in the storage device 130.

According to embodiments of the invention, the calculation circuit 120 may be used to cancel the low-frequency noise of the second ECG signal S2, e.g. motion noise. The motion noise may comprise the noise which is generated when the respondent walks, breathes, or runs, or generated when the wire or electrode placed on the respondent is moved, but the invention should not be limited thereto. Details for the operations of the calculation circuit 120 will be illustrated below.

According to an embodiment of the invention, after the calculation circuit 120 starts to receive the second ECG signal S2, the first calculation circuit 121 of the calculation circuit 120 obtain a QRS template signal $S_{QRS}$ from the second ECG signal S2 received during the initial period (e.g. 0 s~12 s, but the invention should not be limited thereto). That is to say, the calculation circuit 120 may use the first calculation circuit 121 to obtain the QRS template signal $S_{QRS}$ corresponding to the Q-wave signal, R-wave signal and S-wave signal (abbreviated to QRS wave signal below) of the ECG signal of the respondent first, and then perform later operations Specifically, for obtaining the QRS template signal, the first calculation circuit 121 may perform a SWT algorithm for the second ECG signal S2 received in the initial period (e.g. 0 s~12 s, but the invention should not be limited thereto). After the SWT algorithm is performed for the second ECG signal S2 received in the initial period, the second ECG signal S2 received in the initial period may be changed to a plurality levels of ECG signals. That is to say, after the SWT algorithm is performed for the second ECG signal S2 received in the initial period, the second ECG signal S2 may be divided into the ECG signal with different frequencies. In the SWT algorithm, the ECG signal in the lower level corresponds to the part of higher frequency of the ECG signal S2, and the ECG signal in higher level corresponds to the part of lower frequency of the ECG signal S2. For example, if in the embodiment, the 5 levels SWT algorithm is performed, the second ECG signal S2 in the first level (the lowest level) may correspond to the part of the ECG signal S2 with the highest frequency, and the second ECG signal S2 in the fifth level (the highest level) may correspond to the part of the ECG signal S2 with the lowest frequency.

After the SWT algorithm is performed for the second ECG signal S2 received in the initial period, the first calculation circuit 121 may obtain the second ECG signal S2 received in the initial period in the lowest level, and perform a QRS detection for the second ECG signal S2 received in the initial period in the lowest level to generate a QRS template signal $S_{QRS}$. The QRS detection in the embodiment may be the normal detection technologies for the Q-wave signal, R-wave signal and S-wave signal. The normal detection technologies for the Q-wave signal, R-wave signal and S-wave signal can be used to detect the Q-wave signal, R-wave signal and S-wave signal in the second ECG signal S2 received in the initial period in the lowest level. It should be noted that because in the embodiment, only the second ECG signal S2 in the lowest level needs to be obtained, the levels of the SWT algorithm will not be limited.

The QRS template signal $S_{QRS}$ generated by the first calculation circuit 121 will be provided to the second calculation circuit 125 for the later operations of determining the QRS wave signal.

After the initial period, the first SWT circuit 122 may start to receive the second ECG signal S2. The first SWT circuit 122 may perform an SWT algorithm with the first number of levels on the received second ECG signal S2. According to an embodiment of the invention, the first number of levels may be one of the levels which is 8 or higher than 8 (i.e. 8 levels of higher than 8 levels). That is to say, the first SWT circuit 122 may perform an SWT algorithm with 8 or more levels, but the invention should not be limited thereto.

After the SWT algorithm with the first number of levels is performed on the received second ECG signal S2, the first SWT circuit 122 may filter the second ECG signal S2 in the highest level (i.e. the second ECG signal S2 with the lowest frequency is filtered). That is to say, the value of the second ECG signal S2 in the highest level will be 0. For example, if the first number of levels is 8 (i.e. 8 levels), the first SWT circuit 122 may filter the second ECG signal S2 in the eighth level.

After the second ECG signal S2 is processed by the first SWT circuit 122, the first SWT circuit 122 may output the third ECG signals S3 with the first number of levels to the ISWT circuit 123.

According to an embodiment of the invention, the ISWT circuit 123 may perform ISWT algorithm on the third ECG signals S3 with the first number of levels to generate a fourth ECG signal S4 and transmit the fourth ECG signal S4 to the second SWT circuit 124.

According to an embodiment of the invention, the second SWT circuit 124 may perform a SWT algorithm with the second number of levels on the fourth ECG signal S4. According to a preferred embodiment of the invention, the second number of levels may one of 5-8 (i.e. 5-8 levels). That is to say, the second SWT circuit 124 may perform a SWT algorithm with 5 levels, 6 levels, 7 levels or 8 levels, but the invention should not be limited thereto. After the fourth ECG signal S4 is processed by the second SWT circuit 124, the second SWT circuit 124 may output the fifth ECG signals S5 with the second number of levels to the second calculation circuit 125. For example, if the second SWT circuit 124 performs an SWT algorithm with 5 levels on the fourth ECG signal S4, then fifth ECG signals S5 with 5 levels will be generated after the fourth ECG signal S4 is processed by the second SWT circuit 124.

According to an embodiment of the invention, after the second calculation circuit 125 receives the QRS template signal $S_{QRS}$ and the fifth ECG signals S5 with the second number of levels, the second calculation circuit 125 may perform a correlation calculation for the QRS template signal $S_{QRS}$ and the fifth ECG signal S5 in the lowest level to find the Q-wave signal, R-wave signal and S-wave signal (i.e. QRS wave signal) in the fifth ECG signal S5 in the lowest level. Specifically, the second calculation circuit 125 may compare the QRS template signal $S_{QRS}$ to the fifth ECG signal S5 in the lowest level. Then, the second calculation circuit 125 may regard the parts of the fifth ECG signal S5 in the lowest level whose correlation with the QRS template signal $S_{QRS}$ is higher than a threshold (e.g. 0.7, but the invention should not be limited thereto) as the QRS wave signals of the fifth ECG signal S5 in the lowest level. With the relationship that the ESG signals in each level have the corresponding positions, when the second calculation circuit 125 has found the QRS wave signals of the fifth ECG signal S5 in the lowest level, the second calculation circuit 125 can remove the QRS wave signals of the fifth ECG signal S5 in all levels according to the positions of the QRS wave signals of the fifth ECG signal S5 in the lowest level. For example, if the second number of levels is 5 (i.e. 5 levels), the second calculation circuit 125 may remove the QRS wave signals of the fifth ECG signal S5 in first level~fifth level according the positions of all QRS wave signals of the fifth ECG signal S5 in the first level.

Then, the second calculation circuit 125 may perform a PT-wave removal operation on the fifth ECG signals S5 with lower frequencies whose QRS wave signals have been removed to filter the P-wave signals and the T-wave signals in the fifth ECG signals S5 with lower frequencies. In the embodiment, the fifth ECG signals S5 with lower frequencies may be regarded as the fifth ECG signals S5 in the higher levels. For example, if the second number of the levels is 5 (i.e. 5 levels), the fifth ECG signals S5 in the third level~fifth level may be regarded the part of fifth ECG signals S5 with lower frequencies. In addition, in the PT-wave removal operation, any technologies for identifying the P-wave signal and the T-wave signal (e.g. PT threshold algorithm, but the invention should not be limited thereto) can be adopted to detect the P-wave signals and the T-wave signals in the fifth ECG signals S5 with lower frequencies in order to filter the P-wave signals and the T-wave signals in the fifth ECG signals S5 with lower frequencies. After the P-wave signals and the T-wave signals in the fifth ECG signals S5 with lower frequencies have been filtered, the second calculation circuit 125 may perform ISWT algorithm on the remaining fifth ECG signals S5 to generate a noise signal $S_{noise}$. Then, the second calculation circuit 125 may transmit the noise signal $S_{noise}$ to the subtraction circuit 126.

According to an embodiment of the invention, the subtraction circuit 126 may receive the fourth ECG signal S4 from the filter 120 and receive the noise signal $S_{noise}$ from the second calculation circuit 125. In addition, the subtraction circuit 126 may subtract the noise signal $S_{noise}$ from the fourth ECG signal S4 to generate a denoise first (original) ECG signal $S_{denoise}$.

Accordingly, the ECG noise-filtering device 100 provided in the embodiments of the invention can filter the high-frequency noise signal and the low-frequency in the original ECG signal (i.e. the first ECG signal S1).

Figure 3:
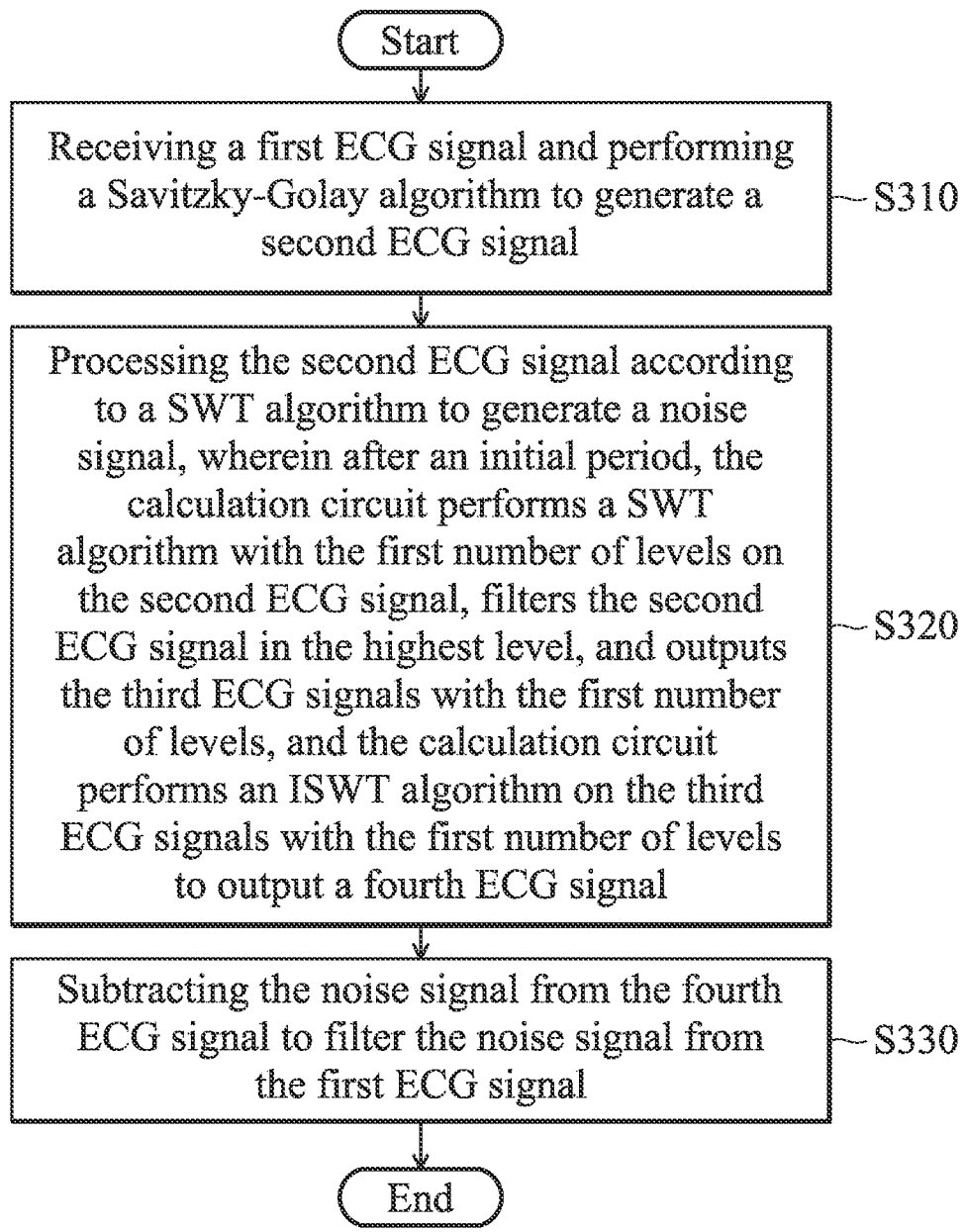
FIG. 3 is a flow chart illustrating an ECG noise-filtering method according to an embodiment of the invention.

FIG. 3 is a flow chart illustrating an ECG noise-filtering method according to an embodiment of the invention. The ECG noise-filtering method can be applied to the ECG noise-filtering device 100. As shown in FIG. 3, in step S310, a filter of the ECG noise-filtering device 100 receives a first ECG signal and performs a Savitzky-Golay algorithm to generate a second ECG signal.

In step S320, a calculation circuit of the ECG noise-filtering device 100 processes the second ECG signal according to a stationary wavelet transform (SWT) algorithm to generate a noise signal, wherein after an initial period, the calculation circuit of the ECG noise-filtering device 100 performs a SWT algorithm with the first number of levels on the second ECG signal, filters the second ECG signal (has been processed through the SWT algorithm with the first number of levels) in the highest level, and outputs the third ECG signals with the first number of levels. In addition, the calculation circuit of the ECG noise-filtering device 100 performs an ISWT algorithm on the third ECG signals with the first number of levels to output a fourth ECG signal.

According to an embodiment of the invention, in step S320 of the ECG noise-filtering method, the calculation circuit of the ECG noise-filtering device 100 may further perform a SWT calculation on the second ECG signal according to the SWT algorithm to obtain the second ECG signal in the lowest level. Then, the calculation circuit of the ECG noise-filtering device 100 performs a QRS detection on the second ECG signal in the lowest level to generate a QRS template signal.

According to an embodiment of the invention, in step S320 of the ECG noise-filtering method, the calculation circuit of the ECG noise-filtering device 100 may further performs a SWT algorithm with the second number of levels on the fourth ECG signal to generate fifth ECG signals with the second number of levels.

According to an embodiment of the invention, in step S320 of the ECG noise-filtering method, the calculation circuit of the ECG noise-filtering device 100 may further perform a correction calculation on the QRS template signal and the fifth ECG signal in the lowest level to filter the QRS wave signals in the fifth ECG signal in each level.

According to an embodiment of the invention, in step S320 of the ECG noise-filtering method, the calculation circuit of the ECG noise-filtering device 100 may further perform a PT-wave removal operation on the fifth ECG signals with lower frequencies whose QRS wave signals have been filtered (or removed) to filter the P-wave signals and the T-wave signals in the fifth ECG signals with lower frequencies.

According to an embodiment of the invention, in step S320 of the ECG noise-filtering method, after filtering the P-wave signals and the T-wave signals in the fifth ECG signals with lower frequencies, the calculation circuit of the ECG noise-filtering device 100 may further perform an ISWT algorithm to generate a noise signal.

In step S330, the calculation circuit of the ECG noise-filtering device 100 may subtract the noise signal from the fourth ECG signal to filter the noise signal from the first (original) ECG signal.

According to an embodiment of the invention, the first number of levels is 8 or higher than 8 (i.e. 8 levels or higher than 8 levels) and the second number of levels is one of 5-8 (i.e. 5 levels~8 levels).

According to the ECG noise-filtering device and method of the invention, the Savitzky-Golay algorithm and the SWT algorithm are combined to filter the irregular noise signals with high frequency or low frequency, e.g. the EMG noise, the wire motion noise, base-line-wander noise, and so on, to recover the original ECG signal. Furthermore, according to the application of the SWT algorithm in the ECG noise-filtering device and method of the invention, the ECG signal can be analyzed more immediately.

Use of ordinal terms such as "first", "second", "third", etc., in the disclosure and claims is for description. It does not by itself connote any order or relationship.

The steps of the method described in connection with the aspects disclosed herein may be embodied directly in hardware, in a software module executed by a processor, or in a combination of the two. A software module (e.g., including executable instructions and related data) and other data may reside in a data memory such as RAM memory, flash memory, ROM memory, EPROM memory, EEPROM memory, registers, a hard disk, a removable disk, a CD-ROM, or any other form of computer-readable storage medium known in the art. A sample storage medium may be coupled to a machine such as, for example, a computer/processor (which may be referred to herein, for convenience, as a "processor") such that the processor can read information (e.g., code) from and write information to the storage medium. A sample storage medium may be integral to the processor. The processor and the storage medium may reside in an ASIC. The ASIC may reside in user equipment. Alternatively, the processor and the storage medium may reside as discrete components in user equipment. Moreover, in some aspects any suitable computer-program product may comprise a computer-readable medium comprising codes relating to one or more of the aspects of the disclosure. In some aspects a computer program product may comprise packaging materials.

The above paragraphs describe many aspects. Obviously, the teaching of the invention can be accomplished by many methods, and any specific configurations or functions in the disclosed embodiments only present a representative condition. Those who are skilled in this technology will understand that all of the disclosed aspects in the invention can be applied independently or be incorporated.

While the invention has been described by way of example and in terms of preferred embodiment, it should be understood that the invention is not limited thereto. Those who are skilled in this technology can still make various alterations and modifications without departing from the scope and spirit of this invention. Therefore, the scope of the present invention shall be defined and protected by the following claims and their equivalents.

What is claimed is:

1. An Electrocardiography (ECG) noise-filtering device, comprising:
    a filter, receiving a first ECG signal and performing an algorithm to generate a second ECG signal; and
    a calculation circuit, coupled to the filter to receive the second ECG signal,
    wherein the calculation circuit comprises:
        a first calculation circuit, coupled to the filter, wherein after the first calculation circuit receives the second ECG signal, the first calculation circuit performs a Stationary Wavelet Transform (SWT) algorithm calculation on the second ECG signal obtained during an initial period, obtains the second ECG signal obtained in the initial period in the lowest level, and performs a QRS detection on the second ECG signal obtained in the initial period in the lowest level to generate a QRS template signal;
        a second calculation circuit, coupled to the first calculation circuit to receive the QRS template signal, wherein the second calculation circuit performs a correlation calculation, a PT-wave removal operation and an inverse SWT (ISWT) algorithm for the QRS template signal to generate a noise signal; and
        a subtraction circuit, coupled to the second calculation circuit, wherein the subtraction circuit subtracts the noise signal from the second ECG signal to filter the noise signal in the first ECG signal.

2. The ECG noise-filtering device of claim 1, wherein the filter is a Savitzky-Golay filter.

3. The ECG noise-filtering device of claim 1, wherein the calculation circuit further comprises:
    a first SWT circuit, coupled to the filter, wherein after the initial period, the first SWT circuit performs the SWT algorithm with a first number of levels on the second ECG signal received from the filter, and filters the second ECG signal in the highest level to output third ECG signals with the first number of levels.

4. The ECG noise-filtering device of claim 3, wherein the calculation circuit further comprises:
    an inverse SWT (ISWT) circuit, coupled to the first SWT circuit to receive the third ECG signals with the first number of levels, wherein the ISWT circuit performs an ISWT algorithm on the third ECG signals with the first number of levels to output a fourth ECG signal.

5. The ECG noise-filtering device of claim 4, wherein the calculation circuit further comprises:
a second SWT circuit, coupled to the ISWT circuit to receive the fourth ECG signal, wherein the second SWT circuit performs the SWT algorithm with a second number of levels on the fourth ECG signal to generate fifth ECG signals with the second number of levels.

6. The ECG noise-filtering device of claim 5,
wherein the second calculation circuit is further coupled to the second SWT circuit to receive the fifth ECG signals with the second number of levels, wherein the second calculation circuit performs the correlation calculation on the QRS template signal and the fifth ECG signal in the lowest level to filter QRS wave signals of fifth ECG signals in each level.

7. The ECG noise-filtering device of claim 6, wherein in the correlation calculation, the second calculation circuit compares the QRS template signal to the fifth ECG signal in the lowest level, wherein the second calculation circuit regards parts of the fifth ECG signal in the lowest level whose correlation with the QRS template signal is higher than a threshold as the QRS wave signals of the fifth ECG signal in the lowest level.

8. The ECG noise-filtering device of claim 6, wherein the second calculation circuit performs the PT-wave removal operation on the fifth ECG signals with lower frequencies whose QRS wave signals have been removed to filter P-wave signals and T-wave signals in the fifth ECG signals with lower frequencies.

9. The ECG noise-filtering device of claim 8, wherein after the second calculation circuit filters the P-wave signals and the T-wave signals in the fifth ECG signals with lower frequencies, the second calculation circuit perform the ISWT algorithm to generate the noise signal.

10. The ECG noise-filtering device of claim 9,
wherein the subtraction circuit receives the fourth ECG signal and the noise signal, and subtracts the noise signal from the fourth ECG signal to filter the noise signal of the first ECG signal.

\* \* \* \* \*